(12) United States Patent  
Fujimoto et al.

(10) Patent No.: US 7,460,635 B2
(45) Date of Patent: Dec. 2, 2008

(54) X-RAY CT APPARATUS, METHOD OF CONTROLLING THE SAME, AND PROGRAM

(75) Inventors: Ryosuke Fujimoto, Tokyo (JP); Uwe Wiedmann, Buc (FR); Emmanuel Lafite, Le Vésinet (FR); Patrick Chrétien, Issy les Moulineaux (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/961,668

(22) Filed: Dec. 20, 2007

(65) Prior Publication Data

US 2008/0152073 A1 Jun. 26, 2008

(30) Foreign Application Priority Data

Dec. 25, 2006 (JP) ............................. 2006-347313

(51) Int. Cl.
*G01N 23/00* (2006.01)
*H05G 1/60* (2006.01)
(52) U.S. Cl. .................... 378/8; 378/5; 378/16
(58) Field of Classification Search ............ 378/4, 378/5, 8, 13, 15, 16, 20
See application file for complete search history.

(56) References Cited

U.S. PATENT DOCUMENTS

| 5,521,955 | A |   | 5/1996 | Gohno et al. |
| 5,530,735 | A |   | 6/1996 | Gard et al. |
| 5,590,165 | A |   | 12/1996 | Gohno et al. |
| 7,039,163 | B2 |  | 5/2006 | Popescu et al. |
| 2003/0152189 | A1 | * | 8/2003 | Li et al. ................... 378/8 |
| 2006/0222142 | A1 | * | 10/2006 | Kudo .......................... 378/4 |

FOREIGN PATENT DOCUMENTS

JP 2006-006531 1/2006
JP 2006-187453 7/2006

* cited by examiner

*Primary Examiner*—Hoon Song
(74) *Attorney, Agent, or Firm*—Armstrong Teasdale LLP

(57) ABSTRACT

In an X-ray CT apparatus for sequentially performing first and second scans of different control parameters by switching the control parameter of at least one of tube voltage and tube current of an X-ray tube on the same slice in a subject, the time interval between the first and second scans is shortened. A scan controller for performing a control on a whole scan starts transmitting the control parameter corresponding to the second scan to an X-ray controller for controlling the tube voltage and the tube current in an X-ray tube during the first scan without waiting for the end of the first scan (S27).

20 Claims, 4 Drawing Sheets

(b)

(a)

X-RAY CT APPARATUS, METHOD OF CONTROLLING THE SAME, AND PROGRAM

CROSS REFERENCE TO RELATED APPLICATIONS

This application claims the benefit of Japanese Patent Application No. 2006-347313 filed Dec. 25, 2006.

BACKGROUND OF THE INVENTION

The field of the present invention relates to an X-ray CT (Computed Tomography) apparatus, a method of controlling the same, and a program. More particularly, the invention relates to an X-ray CT apparatus for sequentially performing a first scan and a second scan using different tube voltages or different tube currents by switching tube voltage or tube current of an X-ray tube, on the same slice in a subject, a method of controlling the same, and a program for the same.

Hitherto, as a scan method of an X-ray CT apparatus, for example, there is a known method of performing a scan by applying two kinds of X-rays using different tube voltages of an X-ray tube, that is, X-ray energy distributions different from each other to a subject. By the scan, two kinds of slice images of the same slice in a subject in which contrast appears different according to the kind of a tissue as a component of the subject are acquired. A subtracting process is executed on the two kinds of images to obtain a differential image in which a specific tissue is emphasized or from which a specific tissue is eliminated.

An example of the scan method for acquiring two kinds of images is a method disclosed in Japanese Unexamined Patent Publication No. 2006-187453. A plurality of data collecting systems each made of an X-ray tube and an X-ray detector are mounted on an X-ray CT apparatus. Tube voltages different from each other are set in the X-ray tubes, and the same slice in the subject is scanned simultaneously by the data collecting systems (first scan method). According to another method described in Japanese Unexamined Patent Publication No. 2006-006531, first and second scans using different tube voltages are performed by switching the tube voltage of the X-ray tube on the same slice in the subject (second scan method).

In the case of comparing the two kinds of images, desirably, a change in the flow of a contrast agent in the subject and body motions caused by heart beat, breathing, and the like are small in two slice images obtained by scanning an almost the same position in a subject with two kinds of different tube voltages.

In the first scan method, the subject is scanned simultaneously with two kinds of X-rays, so that there is no change in the flow of the contrast agent in the subject and no body motion caused by heart beat, breathing, and the like in the acquired two kinds of images. Therefore, from the above-described viewpoint, it can be said that the first scan method is ideal. On the other hand, there are drawbacks such that the first scan method cannot be applied to an existing X-ray CT apparatus having only one data collecting system made of the X-ray tube and the X-ray detector or, when two or more data collecting systems each made of an X-ray tube and an X-ray detector are mounted, the cost largely increases.

On the other hand, the second scan method has advantages such that the method can be applied to an existing X-ray CT apparatus having only one data collecting system made of an X-ray tube and an X-ray detector and modification in hardware is hardly required, so that cost does not increase. Recently, time required for a scan is getting shorter. The shortest time is about 0.35 second. It is therefore becoming almost unnecessary to consider the influence of performing a scan two times at different timings on the demand for reducing a change in flow of the contrast agent in the subject and the body motion.

SUMMARY OF THE INVENTION

Generally, in the case of switching the tube voltage or tube current of an X-ray tube, a scan controller for controlling the whole scan performs a predetermined communication with an X-ray tube controller for controlling tube voltage and tube current of an X-ray tube in a state where no scan is performed to transmit signals of control parameters such as tube voltage and tube current to be set to the X-ray tube controller. The X-ray tube controller sets the tube voltage and the tube current of the X-ray tube on the basis of the control parameters.

However, time required for such communication is long relative to time required for a scan. For example, when the rotation speed of a rotary unit of a scan gantry in which the data collecting system is mounted is about 0.35 (second/rotation), the time required for a half scan is about 0.23 second (=0.35×(⅔)). On the other hand, the time required for communication can be estimated as about 0.15 to 0.20 second or longer. That is, when the tube voltage or tube current is switched by the general sequence in the second scan method, unignorable communication time exists between the end of the first scan and the start of the second scan. There is consequently a problem such that, in practice, a subject to be radiographed is limited to a stationary matter for experiment, an organ which hardly moves, and the like.

From the viewpoint of efficiently processing X-ray projection data obtained by a scan, to prevent the rotary unit of the scan gantry from uselessly rotating and to start the second scan at the same angle as that of the first scan, the permissible time between the end of the first scan and the start of the second scan is about 0.12 second (=0.35−0.23) in the above-described example. Consequently, in a general sequence in which the scan controller and the X-ray tube controller perform a communication between first and second scans and the tube voltage is set, and the like, after completion of the first scan, the second scan cannot be started without uselessly rotating the rotary unit of the scan gantry.

Further, there is the possibility that a method of making not only the tube voltage but also the tube current of the X-ray tube in the first scan and those in the second scan different from each other is executed in future.

In view of the circumstances, an object of the present invention is to provide an X-ray CT apparatus realizing shorter time interval between first and second scans at the time of sequentially performing first and second scans using different tube voltages and/or tube currents by switching at least one of the tube voltage and the tube current of the X-ray tube on the same slice in a subject, a method of controlling the X-ray CT apparatus, and a program for the method.

Means for Achieving the Subject. According to a first aspect, the present invention provides an X-ray CT apparatus including: a rotary unit including an X-ray tube and an X-ray detector for detecting an X-ray emitted from the X-ray tube, the X-ray tube and the X-ray detector being provided while sandwiching a cavity in which a subject is carried, and rotating around the cavity; X-ray tube control means for controlling tube voltage and tube current of the X-ray tube; and scan control means for sequentially performing a first scan and a second scan using different control parameters of at least one of the tube voltage and the tube current of the X-ray tube, on the same slice in an image acquisition space of the cavity by controlling the rotary unit and the X-ray tube control means.

The scan control means starts transmitting at least one control parameter corresponding to the second scan to the X-ray tube control means during the first scan.

According to a second aspect, the present invention provides an X-ray CT apparatus according to claim 1, wherein the scan control means starts preheating a filament in the X-ray tube for obtaining tube current corresponding to the second scan almost simultaneously with completion of the first scan.

In a third aspect, the invention provides the X-ray CT apparatus according to the first or second aspect, wherein the scan control means makes the same a scan start angle in the rotary unit in the first scan and that in the second scan.

In a fourth aspect, the invention provides the X-ray CT apparatus according to the first or second aspect, wherein the scan control means makes scan start timings in the first and second scans synchronize with the same phase of heart beat of the subject.

In a fifth aspect, the invention provides a method of controlling an X-ray CT apparatus for sequentially performing a first scan and a second scan using different control parameters of at least one of the tube voltage and the tube current of the X-ray tube on the same slice in an image acquisition space in the cavity by controlling: a rotary unit including an X-ray tube and an X-ray detector for detecting an X-ray emitted from the X-ray tube, the X-ray tube and the X-ray detector being provided while sandwiching a cavity in which a subject is carried and rotating around the cavity; and X-ray tube control means for controlling the tube voltage and the tube current of the X-ray tube, wherein the method comprises a step of starting transmission of at least one control parameter corresponding to the second scan to the X-ray tube control means during the first scan.

In a sixth aspect, the invention provides a program for making a computer function as scan control means for sequentially performing a first scan and a second scan using different control parameters of at least one of the tube voltage and the tube current of an X-ray tube, on the same slice in an image acquisition space in a cavity by controlling: a rotary unit including the X-ray tube and an X-ray detector for detecting an X-ray emitted from the X-ray tube, the X-ray tube and the X-ray detector being provided while sandwiching the cavity in which a subject is carried and rotating around the cavity; and X-ray tube control means for controlling the tube voltage and the tube current of the X-ray tube, wherein the scan control means starts transmitting at least one control parameter corresponding to the second scan to the X-ray tube control means during the first scan.

The "X-ray tube" has, for example, a filament as a cathode and a target as an anode and generates an X-ray by making thermoelectrons emitted from the filament accelerated by an electric field generated across the electrodes and collide with the target. The filament and the target are made of, for example, tungsten. The target may be of a rotating type or non-rotating type.

The "X-ray detector" is, for example, an X-ray detector of a matrix structure in which X-ray detection elements are arranged two-dimensionally in the rotation direction of the rotary unit and the body axis direction or the carriage direction of the subject, that is, a detector for multi slicing. Alternatively, a single-row X-ray detector in which X-ray detection elements are arranged only in the rotation direction of the rotary unit, that is, a detector for single slicing may be used.

A "scan" denotes a process of rotating the rotary unit while emitting an X-ray to an image acquisition space, detecting an output signal of the X-ray detector every view angle, and collecting X-ray projection data at each view angle. From the viewpoint of shortening the time interval between the first and second scans, the "scan" is preferably a half scan of rotating the rotary unit by 180°+α (α: the angle of a fan of an X-ray beam emitted from the X-ray tube) and collecting X-ray projection data at each view angle. However, placing priority on the picture quality, the scan may be a full scan of rotating the rotary unit by 360° and collecting X-ray projection data at each view angle. The "scan" may be an axial scan performed in a state where a subject is stationary, or a helical scan performed while moving a subject.

In the case of the helical scan, "to sequentially perform first and second scans on the same slice in a subject" denotes to collect X-ray projection data necessary for reconstructing a slice image corresponding to a same slice in the subject.

"Almost simultaneously" in the expression "almost simultaneously with completion of the first scan" denotes, for example, an allowance of about 0.02 second.

The expression ". . . starts preheating a filament in the X-ray tube for obtaining tube current corresponding to the second scan" denotes that control of current to be passed to the filament is started so that target tube current is obtained by a second scan, that is, thermoelectrons of the capacitance corresponding to the tube current are emitted from the filament of the X-ray tube.

The "scan start angle" denotes a view angle at which the rotary unit is rotated and a scan on a subject starts.

The "scan start timing" denotes the timing when the rotary unit is rotated and a scan on a subject starts.

The "heart beat of the subject" can be measured by, for example, cardiography equipment.

In the X-ray CT apparatus of the present invention, at the time of sequentially performing first and second scans using different tube voltages and/or different tube currents by switching at least one of tube voltage and tube current of an X-ray tube on the same slice in a subject, the scan control means starts transmission of the at least one of the control parameters corresponding to the second scan on the X-ray tube control means during the first scan without waiting for the end of the first scan. Consequently, after completion of the first scan, the tube voltage and tube current corresponding to the following second scan can be set earlier. Thus, the time interval between the first and second scans can be further shortened.

DETAILED DESCRIPTION OF THE INVENTION

Best modes for carrying out the present invention will be described below.

Figure 1:
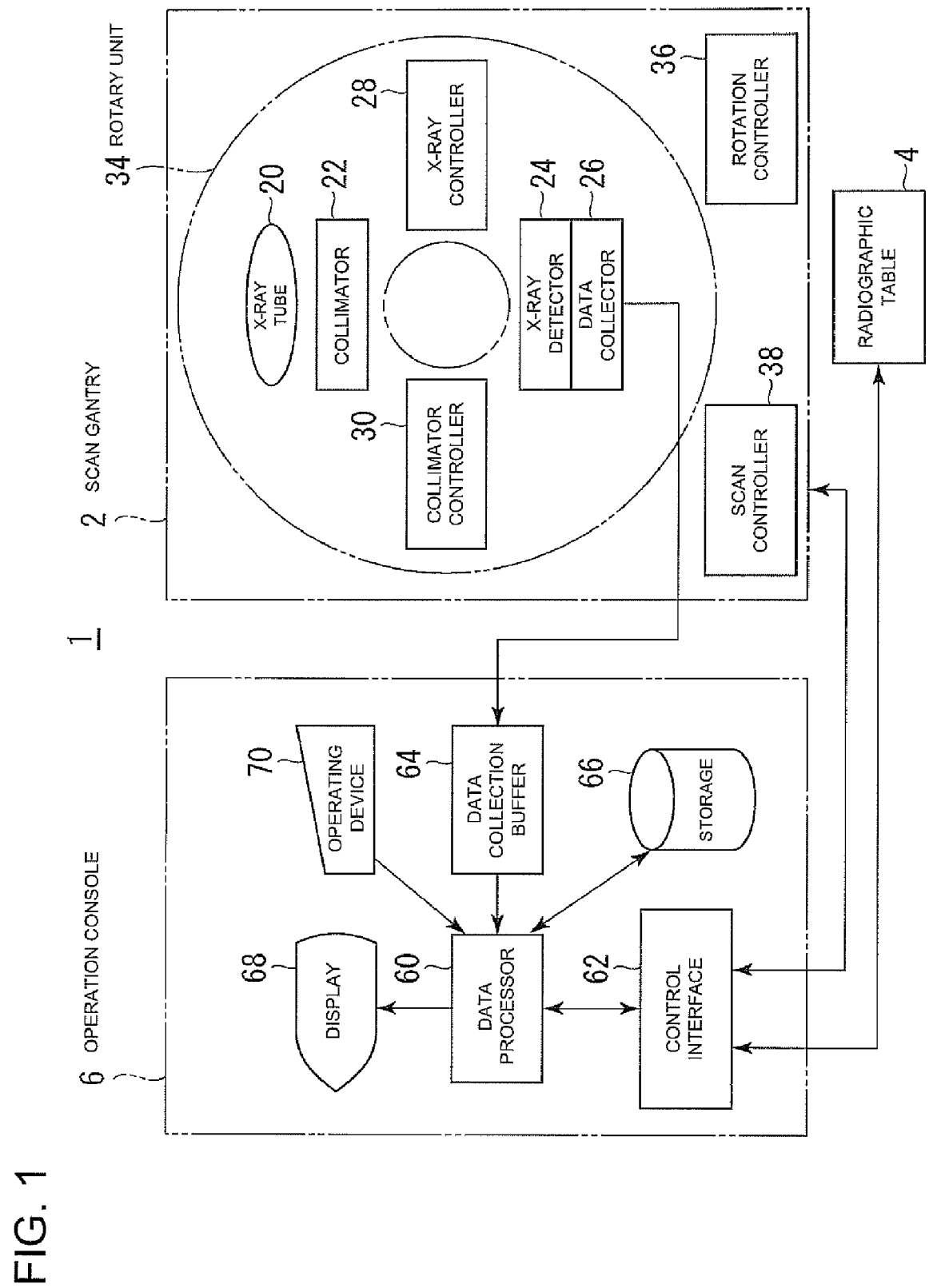
FIG. 1 is a block diagram showing an X-ray CT apparatus as an example of the best mode for carrying out the present invention.

FIG. 1 is a configuration block diagram of an X-ray CT apparatus 1 of an embodiment of the invention. In FIG. 1, the details of the connection relations of the components of the X-ray CT apparatus 1 are not shown.

As shown in FIG. 1, the X-ray CT apparatus 1 has a scan gantry 2, an imaging table 4, and an operation console 6.

The scan gantry 2 has an X-ray tube 20, a collimator 22, an X-ray detector 24, a data collector 26, an X-ray controller 28, a collimator controller 30, a rotary unit 34, a rotation controller 36, and a scan controller 38.

The X-ray tube 20 has a filament as a cathode and a target as an anode and generates an X-ray by making thermoelectrons emitted from the filament accelerated by an electric field generated across the electrodes and collide with the target. The X-ray tube 20 has a grid electrode between the filament and the target. By switching a voltage applied to the grid electrode, generation of the X-ray is controlled. The X-ray tube 20 is an example of the X-ray tube in the present invention.

The collimator 22 shapes the X-ray emitted from the X-ray tube 20 to a corn-shaped X-ray beam, that is, cone-beam X-ray. The cone-beam X-ray is emitted to the X-ray detector 24.

The X-ray detector 24 is a so-called multidetector CT having a plurality of detecting elements arranged in a two-dimensional array in accordance with spread of the cone-beam X-ray. Each of the detecting elements outputs a detection signal according to the intensity of an X-ray detected. The X-ray detector 24 is constructed by, for example, a combination of a scintillator and a photo diode. The X-ray detector 24 is not limited to the configuration but may be a semiconductor X-ray detector using cadmium tellurium (CdTe) or the like, or an X-ray detector of an ion chamber type using xenon (Xe) gas. The X-ray detector 24 is an example of an X-ray detector in the present invention.

Figure 2:
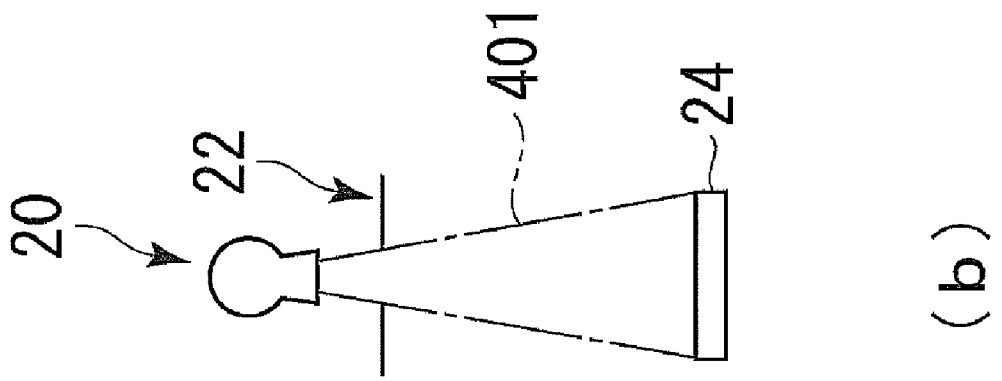
FIGS. 2A and 2B show the relative relations among an X-ray tube, a collimator, and an X-ray detector.
Figure 2:
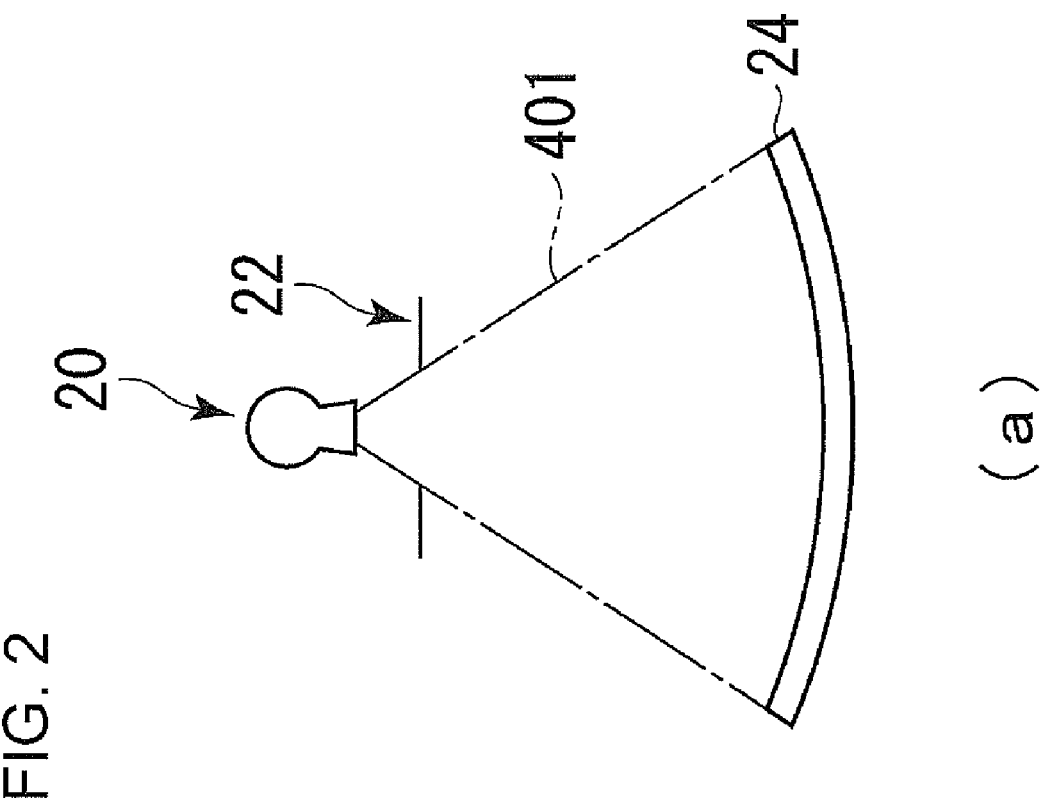

FIGS. 2A and 2B are diagrams showing the interrelation among the X-ray tube 20, the collimator 22, and the X-ray detector 24. FIG. 2A is a diagram showing a state viewed from the front face of the scan gantry 2, and FIG. 2B is a diagram showing a state viewed from a side face. As shown in the diagrams, an X-ray emitted from the X-ray tube 20 is shaped to a cone-beam X-ray 401 by the collimator 22, and the cone-beam X-ray is emitted to the X-ray detector 24.

FIG. 2A shows broadening in one direction of the cone-beam X-ray 401, and this direction is also called a width direction. The width direction of the cone-beam X-ray 401 coincides with the arrangement direction of the channels in the X-ray detector 24. FIG. 2B shows broadening in the other direction of the cone-beam X-ray 401, and this direction is also called a thickness direction. The thickness direction of the cone-beam X-ray 401 coincides with the arrangement direction of the plurality of detection elements in the X-ray detector 24.

The data collector 26 is connected to the X-ray detector 24 and collects detection signals of the detecting elements constructing the X-ray detector 24 as digital data. The detection signals of the detecting elements are signals showing projection of a subject by the X-ray and will be called X-ray projection data.

The X-ray controller 28 controls, mainly, the tube voltage, tube current, and irradiation of an X-ray of the X-ray tube 20 on the basis of signals of control parameters transmitted from the scan controller 38 which will be described later. The X-ray controller 28 is connected to the filament, the target, and the grid electrode of the X-ray tube 20. The X-ray controller 28 controls current passed to the filament to set the filament at a predetermined temperature so that thermoelectrons of capacitance corresponding to the tube current are emitted from the filament. The X-ray controller 28 also controls a voltage to be applied to the filament and the target so as to obtain a target tube voltage. The X-ray controller 28 controls a bias voltage mainly applied to the grid electrode so that an X-ray is emitted at target timing and in target time. That is, by controlling whether an electron beam is generated from the filament or not, whether an X-ray is emitted or not is controlled. More concretely, the X-ray controller 28 switches the bias voltage supplied to the grid electrode in two stages of 0V and a predetermined negative voltage by a not-shown switch. The negative voltage has a value at which the electron beam between the filament and the target is blocked. By switching of the switch, whether the electron beam is generated or not can be controlled. In the following, emission of an X-ray by generating the electron beam from the filament will be called start of X-ray emission. Interruption of emission of an X-ray by generating no electron beam from the filament will be called finishing of X-ray emission. The X-ray controller 28 is an example of the X-ray tube control means in the present invention.

The collimator controller 30 controls the aperture of the collimator 22 so as to obtain a cone-beam X-ray having predetermined broadening on the basis of a control signal from the scan controller 38.

The rotary unit 34 includes the X-ray tube 20 and the X-ray detector 24 for detecting the X-ray emitted from the X-ray tube 20, which are provided while sandwiching a cavity in which the subject is carried. The X-ray tube 20 and the X-ray detector 24 rotate around the cavity. In the rotary unit 34, the components from the X-ray tube 20 to the collimator controller 30 are mounted. In some cases, a part of the scan controller 38 is also mounted. The rotary unit 34 is an example of the rotary unit in the present invention.

The rotation controller 36 controls rotation of the rotary unit 34 on the basis of the control signal transmitted from the scan controller 38 which will be described later.

The scan controller 38 controls the data collector 26, the X-ray controller 28, the collimator controller 30, and the rotation controller 36 in the scan gantry 2 to sequentially perform first and second scans using different tube voltages of the X-ray tube 20 on the same slice in the photographic space of the cavity. Therefore, by carrying the subject into the cavity and performing such scans, a plurality of scans with different tube voltages of the X-ray tube 20 can be performed on each of slice positions of the subject. The scan controller 38 is an example of the scan control means of the present invention.

The subject mounted on the radiographic table 4 is carried into the radiographic space of the cavity between the X-ray tube 20 and the X-ray detector 24.

Referring back to FIG. 1, operation console 6 has a data processor 60, a control interface 62, a data collection buffer 64, a storage 66, a display 68, and an operating device 70.

The data processor 60 is constructed by, for example, a computer or the like. To the data processor 60, the control interface 62 is connected. To the control interface 62, the scan gantry 2 and the radiographic table 4 are connected.

The data processor 60 controls the scan controller 38 in the scan gantry 2 and the radiographic table 4. To the data processor 60, the data collection buffer 64 is connected. To the data collection buffer 64, the data collector 26 of the scan gantry 2 is connected. With the configuration, X-ray projection data collected by the data collector 26 is supplied to the data processor 60 via the data collection buffer 64. To the data processor 60, the storage 66 is connected. In the storage 66, the X-ray projection data supplied to the data processor 60 via the data collection buffer 64 and the control interface 62 is stored. A program for the data processor 60 is stored in the storage 66. The program is executed by the data processor 60 to thereby perform the operation of the X-ray CT apparatus 1.

The data processor 60 performs image reconstruction by using the X-ray projection data of a plurality of views collected in the storage 66 via the data collection buffer 64.

Therefore, by performing the image reconstruction using the collected X-ray projection data on each of the first and second scans performed on the same slice position in the subject, two kinds of slice images with different tube voltages of the X-ray tube 20 can be obtained from the same slice in the subject. The data processor 60 performs a subtracting process among pixels corresponding to each other in the two kinds of slice images obtained as described above, thereby generating a differential image. In the differential image, only an image part expressing a predetermined material in a slice image, for example, an image part expressing a soft tissue or bone as a component of the subject is subject to emphasis or deletion. In such a manner, the two kinds of slice images can be compared with each other.

For the image reconstruction, for example, a cone beam image reconstructing algorithm such as Feldkamp algorithm is used and so-called three-dimensional image reconstruction is performed. The image reconstruction algorithm is specifically described in, for example, "Physics and clinical use of X-ray CT" of Radiological Technology Series under the joint editorship of Masami Tsujioka and Kozo Hanai, supervised by Japanese Society of Radiological Technology, Ohmsha Ltd, first edition issued on Feb. 25, 2005, p20 (non-patent document) and "Image Processing Algorithm" of Algorithm Series 2, Tsuneo Saito, Kindai Kagakusha Co., Ltd., first edition issued on Mar. 10, 1993, pp. 167-171.

To the data processor 60, the display 68 and the operating device 70 are connected. The display 68 is a graphic display or the like. The operating device 70 is constructed by a pointing device, a keyboard, and the like.

The display 68 displays a reconstructed image output from the data processor 60, that is, a slice image of the subject, and the other information. The operating device 70 is operated by the operator and enters various instructions, information, and the like to the data processor 60. The operator operates the apparatus interactively using the display 68 and the operating device 70.

The scan gantry 2 has a structure including the X-ray tube 20 and the X-ray detector 24, for example, a cylindrical structure. The X-ray radiation space is formed in the cylindrical structure of the scan gantry 2. The cone beam X-ray 401 passes through a subject 8 and enters the X-ray detector 24. By the X-ray detector 24, a two-dimensional intensity distribution of the transmitted X-ray is detected.

The operation of the X-ray CT apparatus 1 will now be described.

When the operator enters information necessary for image acquisition, for example, the tube voltage and tube current of the X-ray tube, slice thickness, the scan type (axial or helical scan), and the like by using the operating device 70 of the operation console 6 and performs an operation of instructing image acquisition, in response to the operation, the data processor 60 transmits a control signal for image acquisition to the scan controller 38 in the scan gantry 2 and the radiographic table 4 via the control interface 62.

With the radiographic table 4, the top plate of the table on which the subject as an object of radiography is moved on the basis of the control signal from the data processor 60, thereby carrying the subject into the radiographic space of the cavity in the scan gantry 2, that is, the X-ray radiation space. In the case where the scan type is the axial scan, the top plate is repeatedly moved and stopped. In the case where the scan type is the helical scan, the top plate is continuously moved at predetermined speed.

On the other hand, on the basis of the control signal from the data processor 60, the scan controller 38 sends control signals to the X-ray controller 28, the collimator controller 30, and the rotation controller 36 to indirectly control the tube voltage and tube current of the X-ray tube 20, the X-ray irradiation timing and irradiation time, the rotation of the rotary unit 34, and the like.

By the control on the radiographic table 4 and the scan controller 38, a scan is performed. For example, by rotating the rotary unit 34 in a state where the radiographic table 4 is stopped, an axial scan is performed. Alternatively, by continuously moving the top plate of the radiographic table 4 in the boxy axis direction of the subject 8 concurrently with the rotation of the rotary unit 34, the X-ray tube 20 and the X-ray detector 24 mounted in the rotary unit 34 revolute along the helical locus around the subject and relative to the subject. In such a manner, a so-called helical scan is performed. In the helical scan, as described above, the first and second scans using different tube voltages of the X-ray tube are sequentially performed on the same slice in the subject. For example, the different tube voltages are 80 kV and 140 kV.

X-ray projection data of a plurality of (for example, about 1,000) views is collected per scan. The X-ray projection data is collected by a series of the X-ray detector 24, the data collector 26, and the data collection buffer 64.

A sequence in the scan will be described. For easier understanding, a sequence of the embodiment will be described in comparison with a sequence of a comparative example.

Figure 3:
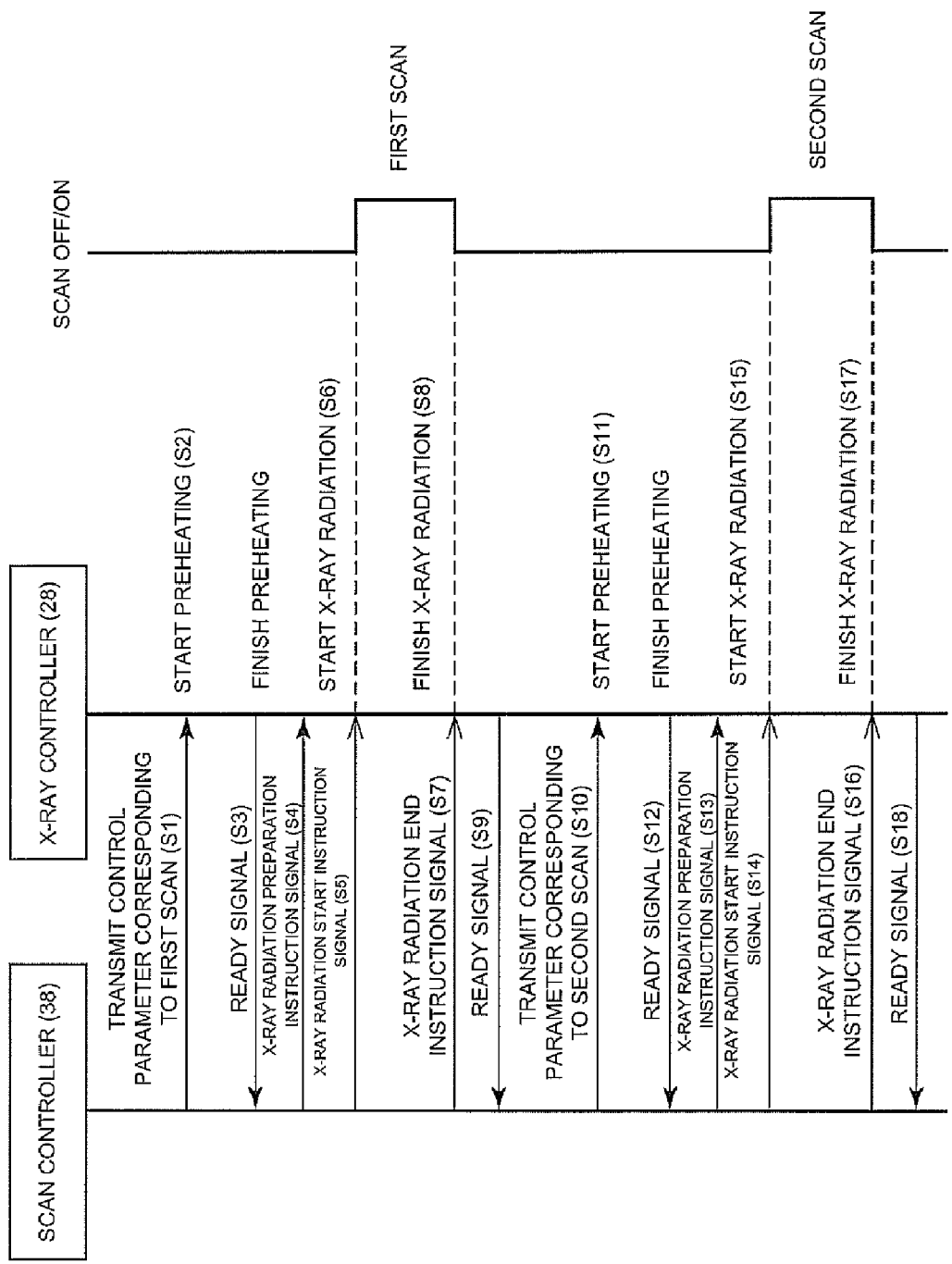
FIG. 3 is a diagram showing a sequence of a comparative example in scans.
Figure 4:
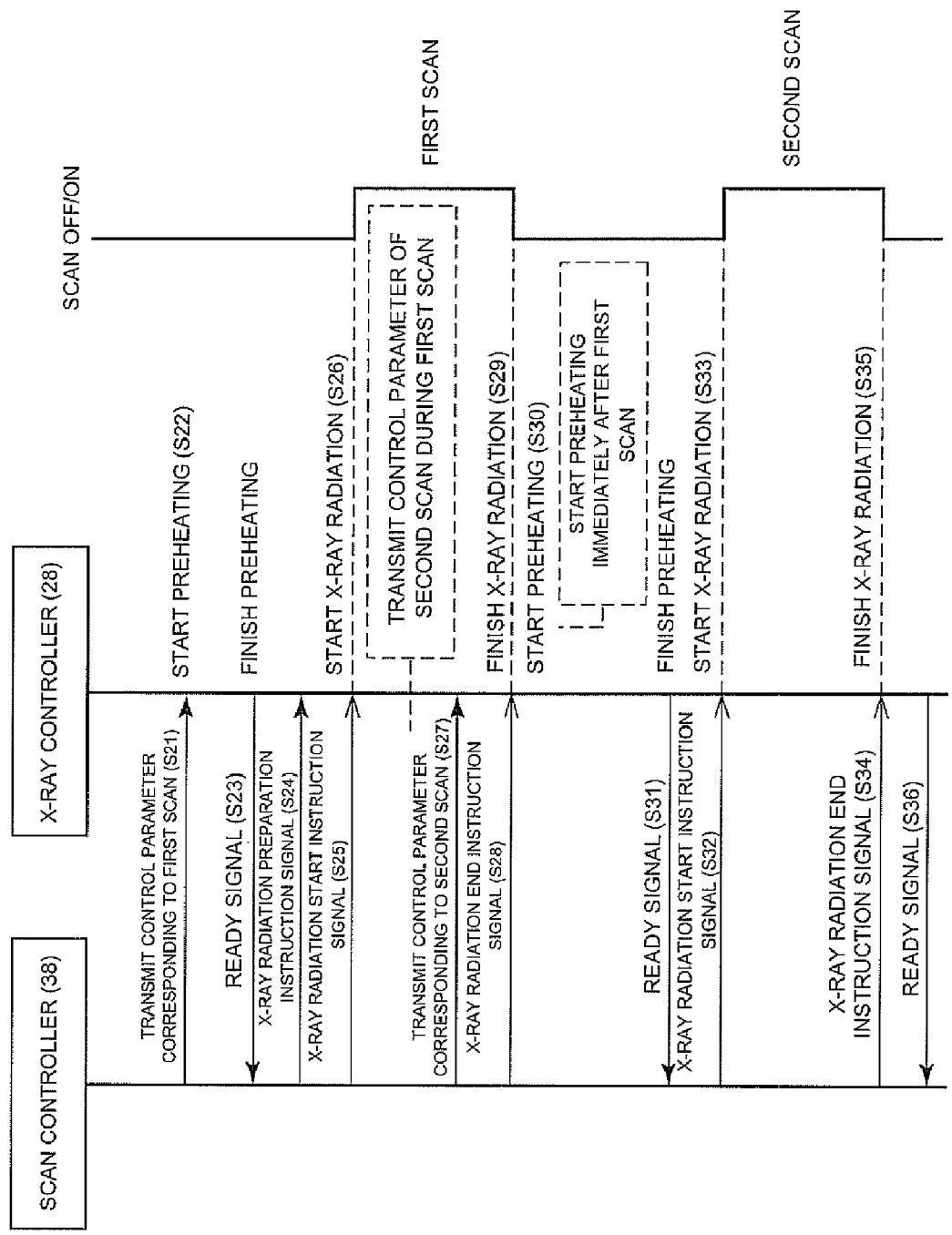
FIG. 4 is a diagram showing a sequence of the embodiment in scans.

FIG. 3 shows a sequence of the comparative example. FIG. 4 is a diagram showing the sequence of the embodiment.

Sequence of Comparative Example. In the case of a comparative example, after completion of the first scan, the scan controller 38 starts transmitting control parameters including the tube voltage and the tube current corresponding to the second scan to the X-ray controller 28.

The operations will be described in order. The scan controller 38 transmits control parameters including the tube voltage and the tube current corresponding to the first scan to the X-ray controller 28 (S1). On the basis of the control parameters, the X-ray controller 28 starts the control of the voltage generator so that the tube voltage corresponding to the first scan is applied to the electrode of the X-ray tube 20, and starts preheating of the filament in the X-ray tube 20 so that the tube current corresponding to the first scan flows at the time of the first scan (S2).

When the voltage applied to the electrode in the X-ray tube 20 reaches a predetermined target voltage and is stabilized and the temperature of the filament reaches a predetermined target temperature and is stabilized, the X-ray controller 28 sends a signal indicative of completion of setting of the tube voltage and the preheating to the scan controller 38 (S3).

The scan controller 38 receives the signal and transmits a signal to instruct X-ray radiation preparation to the X-ray controller 28 (S4).

After that, the scan controller 38 transmits the instruction signal of X-ray radiation start to the X-ray controller 28 by a hardware signal (S5). The X-ray controller 28 receives the instruction signal and switches the voltage to be applied to the grid electrode in the X-ray tube 20 to thereby generate an electron beam from the filament, and start the X-ray radiation (S6). In such a manner, the first scan starts.

After lapse of target radiation time after start of the X-ray radiation, the scan controller 38 transmits an instruction signal to finish the X-ray radiation by a hardware signal to the X-ray controller 28 (S7). On receipt of the instruction signal, the X-ray controller 28 switches the voltage to be applied to the grid electrode of the X-ray tube 20, by interrupting the electron beam from the filament to finish the X-ray irradiation (S8). It ends the first scan.

When the X-ray controller 28 becomes ready for the following control, the X-ray controller 28 transmits a ready signal to the scan controller 38 (S9). It ends the series of sequence processes of the first scan.

After completion of the sequence process on the first scan, the scan controller 38 transmits the control parameters including the tube voltage and the tube current corresponding to the second scan to the X-ray controller 28. Subsequently, the series of sequence processes (S10 to S18) on the second scan similar to those of the first scan are performed.

Sequence of Embodiment. On the other hand, in the case of the sequence of the embodiment, the scan controller 38 starts transmitting the control parameters including the tube voltage and the tube current corresponding to the second scan to the X-ray controller 28 during the first scan.

The operations will be described in order. The scan controller 38 transmits control parameters including the tube voltage and the tube current corresponding to the first scan to the X-ray controller 28 (S21). On the basis of the control parameters, the X-ray controller 28 starts the control of the voltage generator so that the tube voltage corresponding to the first scan is applied to the electrode of the X-ray tube 20, and starts preheating of the filament in the X-ray tube 20 so that the tube current corresponding to the first scan flows at the time of the first scan (S22).

When the voltage applied to the electrode in the X-ray tube 20 reaches a predetermined target voltage and is stabilized and the temperature of the filament reaches a predetermined target temperature and is stabilized, the X-ray controller 28 sends a signal indicative of completion of setting of the tube voltage and the preheating to the scan controller 38 (S23).

The scan controller 38 receives the signal and transmits a signal to instruct X-ray radiation preparation to the X-ray controller 28 (S24).

After that, the scan controller 38 transmits the instruction signal of X-ray radiation start to the X-ray controller 28 by a hardware signal (S25). The X-ray controller 28 receives the instruction signal and switches the voltage to be applied to the grid electrode in the X-ray tube 20 to thereby generate an electron beam from the filament, and start the X-ray radiation. It starts the first scan (S26).

The above operations are the same as those of the sequence of the comparative example. In the embodiment of the invention, the following sequence is characteristic.

During the first scan, that is, without waiting for the end of the first scan, the scan controller 38 starts transmitting the control parameters including the tube voltage and the tube current corresponding to the second scan to the X-ray controller 28 (S27).

The transmission of the control parameters are finished after a short while and after lapse of the target radiation time since the X-ray radiation is started, the scan controller 38 transmits the X-ray radiation end instruction signal by a hardware signal to the X-ray controller 28 (S28). The X-ray controller 28 receives the instruction signal and switches the voltage to be applied to the grid electrode in the X-ray tube, thereby interrupting the electron beam from the filament and finishing the X-ray irradiation. It finishes the first scan (S29). Immediately after that, that is, almost on completion of the first scan, on the basis of the control parameters received in advance during the first scan, the X-ray controller 28 starts the control of the voltage generator so that the tube voltage corresponding to the second scan is applied to the electrode of the X-ray tube 20 and starts the preheating of the filament of the X-ray tube 20 so that the tube current corresponding to the second scan flows in the second scan (S30).

When the voltage applied to the electrode in the X-ray tube 20 reaches a predetermined target voltage and is stabilized and the temperature of the filament reaches a predetermined target temperature and is stabilized, the X-ray controller 28 sends a signal indicative of completion of setting of the tube voltage and the preheating to the scan controller 38 (S31).

After that, the scan controller 38 transmits the instruction signal of X-ray radiation start to the X-ray controller 28 by a hardware signal (S32). The X-ray controller 28 receives the instruction signal and switches the voltage to be applied to the grid electrode in the X-ray tube 20 to thereby generate an electron beam from the filament and start the X-ray radiation. It starts the second scan (S33).

After lapse of target radiation time since the X-ray radiation has started, the scan controller 38 transmits an instruction signal to finish the X-ray radiation by a hardware signal to the X-ray controller 28 (S34). On receipt of the instruction signal, the X-ray controller 28 switches the voltage to be applied to the grid electrode of the X-ray tube 20, interrupts the electron beam from the filament, to finish the X-ray irradiation. It ends the second scan (S35).

When the X-ray controller 28 becomes ready for the next control, the X-ray controller 28 transmits a ready signal to the scan controller 38 (S36).

In each of the scans, the X-ray tube 20 emits an X-ray with the set tube voltage and tube current, and the X-ray detector 24 detects a cone-beam X-ray passed through the subject on the view unit basis. The data collector 26 collects X-ray projection data of the cone-beam X-ray on the view unit basis. The X-ray projection data collected by the data collector 26 is supplied to the data collection buffer 64 and stored in the storage 66.

The data processor 60 performs three-dimensional image reconstruction on the basis of a number of pieces of X-ray projection data including the X-ray projection data of the views stored in the storage 66, thereby generating a slice image in the image acquisition space.

The data processor 60 generates a slice image by the first scan and a slice image by the second scan on the same slice in the subject, and performs a subtracting process on the two kinds of slice images, thereby obtaining a differential image in which a predetermined tissue is emphasized or a predetermined tissue is removed.

The display 68 displays the slice images, the differential image obtained from the slice images, or the like on the screen.

As described above, in the embodiment, at the time of sequentially performing the first and second scans with different tube voltages by switching the tube voltage of the X-ray tube 20 on the same slice in the subject, without waiting for the end of the first scan, that is, during the first scan, the scan controller 38 starts transmitting the control parameters including the tube voltage and the tube current corresponding to the second scan to the X-ray controller 28. Consequently, after completion of the first scan, the tube voltage and tube current corresponding to the following second scan can be set earlier, and the time interval between the first and second scans can be further shortened.

In the embodiment, almost on completion of the first scan, the scan controller 38 starts preheating of the filament of the X-ray tube 20 for obtaining the tube current corresponding to the second scan. Consequently, the timing at which the temperature of the filament is stabilized to a target predetermined temperature becomes earlier. It is advantageous for shortening the time interval between the first and second scans.

In the embodiment, for easier explanation, only the tube voltage is described as the control parameter switched between the first and second scans. For example, obviously, only the tube current or a combination of the tube voltage and the tube current may be employed as the control parameter.

In the embodiment, the scan controller 38 does not control the rotation angle of the rotary unit 34 at the start of the scan. For example, the scan controller may control so that the scan start angle in the first scan and that of the second scan become the same. By the control, the corresponding relations between a position in a data array, the view angle corresponding to a data value in the position, and a position on a projection plane in the X-ray projection data in the first scan and that in the X-ray projection data in the second scan become the same. Consequently, at the time of generating a differential image between a slice image obtained by the first scan and a slice image obtained by the second scan, the subtracting process is performed between two kinds of X-ray projection data (also called raw data) before image reconstruction corresponding to the two kinds of slice images, whose positions in the data array are the same, thereby obtaining the differential data of the X-ray projection data. By performing image reconstruction using the differential data, a target differential image can be generated. That is, it is sufficient to perform a process called image reconstruction requiring relatively long time once, so that the arithmetic process amount of the data processor 60 can be largely reduced. It contributes to lessen the burden on the data processor 60 and increase the processing speed. For example, it is advantageous for the case of performing a so-called real-time process of generating and displaying a slice image almost simultaneously with a scan.

In the case of performing a control of making the scan start angles in the first and second scans the same, when the general sequence is executed, at the time of performing the second scan after completion of the first scan, although the rotary unit 34 is reset to a specific scan start angle, it is not ready for start of a scan. The apparatus may have to wait for the second scan until the rotary unit 34 further rotates and returns again to the specific scan start angle. Therefore, in the case of performing, during the first scan, a combination of a control of starting transmission of control parameters including the tube voltage and the tube current corresponding to the second scan and a control of making the scan start angles in the first and second scans the same on the X-ray controller 28, it is very effective to shorten the time interval between the first and second scans.

In the embodiment, the scan controller 38 does not perform the control of making the scan start timing with something in the first and second scans. For example, the scan start timings in the first and second scans may be controlled to synchronize with the same phase as the heart beat of the subject. By the control, deformation of the heart due to expansion/contraction of the heart of the subject can be reduced.

In the embodiment, two kinds of scans using different tube voltages are performed on the same slice in the image acquisition space. Obviously, scans using three or more kinds of tube voltages may be performed by the number according to the kinds.

From the viewpoint of shortening of the time interval between the first and second scans, desirably, the relation between tube current I1 corresponding to the first scan and tube current I2 corresponding to the second scan satisfies I2≧I1. The temperature of the filament of the X-ray tube does not decrease soon. There is the tendency that it takes longer time to decrease the temperature of the filament than to increase the temperature. Consequently, at the time of shift from the first scan to the second scan, increase in the temperature of the filament is more advantageous for shortening of the time interval between the first and second scans.

From a similar viewpoint, desirably, the relation between tube voltage V1 in the first scan and tube voltage V2 in the second scan satisfies V2≧V1. The voltage generator for applying a voltage to the electrode in the X-ray tube is often a circuit of a type of increasing output voltage by charging a capacitor, and the charges do not easily escape. There is the tendency that it takes longer time to decrease the output voltage than to increase the output voltage. Consequently, at the time of shift from the first scan to the second scan, increase in the tube voltage is more advantageous for shortening of the time interval between the scans.

In the case where it is difficult to simultaneously satisfy both of the desirable relation between the tube voltages in the first and second scans and the desirable relation between the tube currents, by comparing time required to decrease the temperature of the filament and time required to decrease the output voltage of the voltage generator with each other, priority is placed on the condition requiring shorter time. For example, the parameters are set as V1=80 kV, I1=600 mA, V2=140 kV, and I2=400 mA, that is, V2>V1 and I2<I1. Priority is placed on the desirable relation with respect to the tube voltages.

The foregoing embodiments are examples of the best mode for carrying out the present invention, and the present invention is not limited to the embodiments. That is, in the present invention, without departing from the gist of the invention, any change and addition is possible.

A program for making a computer function as an X-ray CT apparatus of the invention or means in the apparatus is also an example of the embodiment of the invention. The program may be supplied by downloading, distribution, or the like via a network such as the Internet. The program may be recorded on a computer-readable recording medium and the recording medium may be supplied.

The invention claimed is:

1. An X-ray CT apparatus comprising:
a rotary unit including an X-ray tube and an X-ray detector for detecting an X-ray emitted from the X-ray tube, the X-ray tube and the X-ray detector being provided while sandwiching a cavity in which a subject is carried, and rotating around the cavity;
an X-ray tube controller for controlling tube voltage and tube current of the X-ray tube; and
a scan controller for sequentially performing a first scan and a second scan using different control parameters of at least one of the tube voltage and the tube current of the X-ray tube, on the same slice in an image acquisition space of the cavity by controlling the rotary unit and the X-ray tube controller,
wherein the scan controller starts transmitting at least one control parameter corresponding to the second scan to the X-ray tube controller during the first scan.

2. The X-ray CT apparatus according to claim 1, wherein the scan controller starts preheating a filament in the X-ray tube for obtaining tube current corresponding to the second scan almost simultaneously with completion of the first scan.

3. The X-ray CT apparatus according to claim 1, wherein the scan controller makes the same a scan start angle in the rotary unit in the first scan and that in the second scan.

4. The X-ray CT apparatus according to claim 2, wherein the scan controller makes the same a scan start angle in the rotary unit in the first scan and that in the second scan.

5. The X-ray CT apparatus according to claim 1, wherein the scan controller makes scan start timings in the first and second scans synchronize with the same phase of heart beat of the subject.

6. The X-ray CT apparatus according to claim 2, wherein the scan controller makes scan start timings in the first and second scans synchronize with the same phase of heart beat of the subject.

7. The X-ray CT apparatus according to claim 3, wherein the scan controller makes scan start timings in the first and second scans synchronize with the same phase of heart beat of the subject.

8. The X-ray CT apparatus according to claim 4, wherein the scan controller makes scan start timings in the first and second scans synchronize with the same phase of heart beat of the subject.

9. The X-ray CT apparatus according to claim 1, wherein at least one control parameter is the tube voltage.

10. The X-ray CT apparatus according to claim 2, wherein at least one control parameter is the tube voltage.

11. A method of controlling an X-ray CT apparatus for sequentially performing a first scan and a second scan using different control parameters of at least one of the tube voltage and the tube current of the X-ray tube, on the same slice in an image acquisition space in the cavity by controlling: a rotary unit including an X-ray tube and an X-ray detector for detecting an X-ray emitted from the X-ray tube, the X-ray tube and the X-ray detector being provided while sandwiching a cavity in which a subject is carried and rotating around the cavity; and an X-ray tube controller for controlling the tube voltage and the tube current of the X-ray tube, wherein the method comprises a step of starting transmission of at least one control parameter corresponding to the second scan to the X-ray tube controller during the first scan.

12. The method of controlling an X-ray CT apparatus according to claim 11, further comprising a step of starting preheating a filament in the X-ray tube for obtaining tube current corresponding to the second scan almost simultaneously with end of the first scan.

13. The method of controlling an X-ray CT apparatus according to claim 11, further comprising a step of making the same a scan start angle in the rotary unit in the first scan and that in the second scan.

14. The method of controlling an X-ray CT apparatus according to claim 11, further comprising a step of making scan start timings in the first and second scans synchronize with the same phase of heart beat of the subject.

15. The method of controlling an X-ray CT apparatus according to claim 11, wherein at least one control parameter is the tube voltage.

16. A computer program product for making a computer function as a scan controller for sequentially performing a first scan and a second scan using different control parameters of at least one of the tube voltage and the tube current of an X-ray tube, on the same slice in an image acquisition space in a cavity by controlling: a rotary unit including the X-ray tube and an X-ray detector for detecting an X-ray emitted from the X-ray tube, the X-ray tube and the X-ray detector being provided while sandwiching the cavity in which a subject is carried and rotating around the cavity; and an X-ray tube controller for controlling the tube voltage and the tube current of the X-ray tube, wherein the scan controller starts transmitting at least one control parameter corresponding to the second scan to the X-ray tube controller during the first scan.

17. The computer program product according to claim 16, wherein the scan controller starts preheating a filament in the X-ray tube for obtaining tube current corresponding to the second scan almost simultaneously with completion of the first scan.

18. The computer program product according to claim 16, wherein the scan controller makes the same a scan start angle in the rotary unit in the first scan and that in the second scan.

19. The computer program product according to claim 16, wherein the scan controller makes scan start timings in the first and second scans synchronize with the same phase of heart beat of the subject.

20. The computer program product according to claim 16, wherein at least one control parameter is the tube voltage.

* * * * *